United States Patent [19]

Kahl et al.

[11] Patent Number: 4,910,332

[45] Date of Patent: Mar. 20, 1990

[54] PROCESS FOR THE PREPARATION OF POLYISOCYANATES CONTAINING URETHANE GROUPS AND THE PRODUCTS OBTAINED

[75] Inventors: Lothar Kahl, Bergisch Gladbach; Josef Pedain, Cologne; Wolfgang Wellner, Bergisch Gladbach, all of Fed. Rep. of Germany

[73] Assignee: Bayer Aktiengesellschaft, Leverkusen, Fed. Rep. of Germany

[21] Appl. No.: 269,230

[22] Filed: Nov. 9, 1988

[30] Foreign Application Priority Data

Nov. 18, 1987 [DE] Fed. Rep. of Germany ....... 3739261

[51] Int. Cl.$^4$ ............................................. C07C 119/48
[52] U.S. Cl. .................................................... 860/351
[58] Field of Search ......................................... 560/351

[56] References Cited

FOREIGN PATENT DOCUMENTS 0154485  3/1982  German Democratic Rep. ..................................... 560/351

Primary Examiner—Alan Siegel
Attorney, Agent, or Firm—Joseph C. Gil; Thomas W. Roy

[57] ABSTRACT

The present invention is directed to a process for the preparation of polyisocyanates containing urethane groups in which the content in monomeric starting diisocyanate is at most 0.4% by weight by reacting in a urethane-forming reaction (a) an excess quantity, based on component (b), of a diisocyanate component containing at least one aromatic diisocyanate which is free from urethane groups with (b) a polyol component containing at least one polyhydric alcohol in the molecular weight range of 62 to about 250 followed by distillative removal of the unreacted excess starting diisocyanate (a), characterized in that before the distillative removal of the excess starting diisocyanate (a) is carried out, (c) an aliphatic polyisocyanate containing isocyanurate groups is incorporated in the urethane-containing reaction product of components (a) and (b) in a quantity of about 0.3 to 10% by weight, based on the undistilled reaction product of components (a) and (b), and the distillation residue is then optionally dissolved in an inert solvent and up to about 0.5 equivalents of an alcohol, per kg of solvent-free distillation residue on a solvent free basis is added to the resulting solution so that the amount of free starting diisocyanate (a) is further reduced and urethane groups are formed.

The present invention is also directed to the polyisocyanates containing urethane groups obtained by this process.

8 Claims, No Drawings

PROCESS FOR THE PREPARATION OF POLYISOCYANATES CONTAINING URETHANE GROUPS AND THE PRODUCTS OBTAINED

BACKGROUND OF THE INVENTION

1. Field of the Invention

This invention relates to a new process for the preparation of urethane group-containing polyisocyanates which contain only a small proportion of monomeric starting diisocyanates and to the products of this process.

2. Description of the Prior Art

Aromatic polyisocyanates containing urethane groups, especially those based on diisocyanatotoluene, are valuable "lacquer polyisocyanates." They are described, for example, in "Lehrbuch der Lacke und Beschichtungen" by H. Kittel, publishers W. A. Colomb, Berlin 1973, Volume I, Part 2. They are generally prepared by the reaction of low molecular weight, polyhydric alcohols with an excess of diisocyanates followed by removal of the excess diisocyanate by distillation or extraction.

In the process of extraction, the excess diisocyanate can be carefully removed by means of suitable solvent mixtures. One important disadvantage of this method is that it requires the use of large quantities of extracting agent which is difficult to subsequently separate, recover and work up such that the process is in most cases uneconomical on a technical scale.

Moreover, extraction removes not only the monomeric diisocyanates but also a proportion of low molecular weight polyisocyanates from the polyisocyanate mixture, thereby altering the properties of the polymer.

Removal of the excess diisocyanate by distillation is most effectively carried out by the method of thin layer distillation but since a polyisocyanate which is free from monomers has a very high softening point and a high fusion viscosity, this distillation must be carried out at temperatures from 160° to 180° C.; however, decomposition and polymerization reactions occur at these temperatures. This in turn leads to the deposition of polymers and severe mechanical strain on the thin layer distillation apparatus.

A simplified method of separating monomers from low molecular weight aromatic polyisocyanates containing urethane groups is described in DE-PS 214,847, in which the polyisocyanates containing urethane groups are modified with aromatic polyisocyanates containing acyl urea, allophanate or biuret structures. After removal of the excess monomeric diisocyanates by extraction or distillation, the polyisocyanate obtained has a low viscosity and high isocyanate content. One major disadvantage of these products, however, is their high content of monomeric diisocyanate, which may be as much as 0.6 to 1.95%, based on solids. This high proportion of free starting diisocyanate severely limits the use of these products in numerous fields for reasons of workplace hygiene.

It has now been found that polyisocyanates containing urethane groups based on aromatic diisocyanates, in particular on diisocyanatotoluene, may be obtained with a low viscosity, a high isocyanate content and a proportion of free starting diisocyanate of not more than 0.4%, preferably 0.3% by weight if the distillative removal of excess monomeric starting diisocyanate is carried out in the presence of aliphatic polyisocyanates containing isocyanurate groups and the product obtained as distillation residue is after-treated, if necessary, with a sub-equivalent quantity of monohydric and/or polyhydric alcohols in the presence of an inert solvent.

SUMMARY OF THE INVENTION

The present invention is directed to a process for the preparation of polyisocyanates containing urethane groups in which the content in monomeric starting diisocyanate is at most 0.4% by weight by reacting in a urethane-forming reaction (a) an excess quantity, based on component (b), of a diisocyanate component containing at least one aromatic diisocyanate which is free from urethane groups with (b) a polyol component containing at least one polyhydric alcohol in the molecular weight range of 62 to about 250 followed by distillative removal of the unreacted excess starting diisocyanate a), characterized in that before the distillative removal of the excess starting diisocyanate (a) is carried out, (c) an aliphatic polyisocyanate containing isocyanurate groups is incorporated in the urethane containing reaction product of components (a) and (b) in a quantity of about 0.3 to 10% by weight, based on the undistilled reaction product of components (a) and (b), and the distillation residue is then optionally dissolved in an inert solvent and up to about 0.5 equivalents of an alcohol, per kg of solvent-free distillation residue on a solvent free basis is added to the resulting solution so that the amount of free starting diisocyanate (a) is further reduced and urethane groups are formed.

The present invention is also directed to the polyisocyanates containing urethane groups obtained by this process.

DETAILED DESCRIPTION OF THE INVENTION

The starting materials (a) may be any aromatic diisocyanates in the molecular weight range of 160 to 300 which are free from urethane groups. 2,4-diisocyanatotoluene and commercial mixtures thereof with 2,6-diisocyanatotoluene are particularly preferred starting components. The mixtures preferably contain up to about 35% by weight of 2,6-diisocyanatotoluene, based on the total quantity of the mixture.

The polyol component (b) may be any polyhydric aliphatic alcohol in the molecular weight range of 62 to about 250. Examples of such alcohols include ethylene glycol, 1,2- and 1,3-dihydroxypropane, 1,2-, 1,3-, 2,3-and 1,4-dihydroxybutane, 1,6-dihydroxyhexane, diethylene glycol, triethylene glycol, dipropylene glycol, neopentyl glycol, 2,2,4-trimethyl-1,3-dihydroxypentane, glycerol, trimethylolethane, trimethylolpropane and mixtures of such polyhydric alcohols. Component (b) preferably is based on mixtures of dihydric alcohols and trihydric alcohols which have molecular weights of 62 to about 250, in particular 90 to about 180. Mixtures of such dihydric and trihydric alcohols in which the molar ratio of diol to triol is about 1:2 to 1:0.5 are particularly preferred. Component (b) could, of course, include small quantities of alcohols which are higher than trifunctional, for example pentaerythritol.

The polyisocyanates containing urethane groups are prepared in known manner by the reaction of component (a) with component (b) in proportions which maintain an NCO/OH equivalent ratio above 2. The NCO-/OH equivalent ratio is preferably about 3:1 to 15:1, especially about 3:1 to 7:1. The reaction is generally carried out within a temperature range of about 60° to 120° C.

Stabilizers may be added to the reaction mixture to avoid side reactions. Examples of suitable stabilizers include inorganic acids and inorganic and organic acid chlorides such as hydrogen chloride, hydrogen bromide, thionyl chloride, sulphuryl chloride, benzoyl chloride, oxalyl chloride, isophthalyl chloride, carbamic acid chlorides and carbamic acid bromides. If stabilizers are used, they are added in quantities of about 100 to 1000 ppm, preferably about 100 to 500 ppm, based on the weight of components (a) and (b).

The reaction products obtained after the reaction of components (a) and (b) are polyisocyanates containing urethane groups together with excess starting diisocyanate (a). According to the invention, an aliphatic polyisocyanate containing isocyanurate groups (c) is added to this mixture, generally in a quantity of about 0.3 to 10% by weight, preferably about 0.5 to 10% by weight based on the weight of the undistilled reaction product.

A particularly suitable aliphatic polyisocyanate containing isocyanurate groups is trimerized 1,6-diisocyanatohexane having an isocyanate content of about 15 to 25% by weight, containing not more than 0.5% by weight, preferably not more than 0.2% by weight of free 1,6-diisocyanatohexane and having a viscosity below 5000 mPa.s/23° C. Polyisocyanates of this kind are preferably N,N,N-tris-(isocyanatohexyl)-isocyanurate or mixtures of this triisocyanate with its higher homologs containing more than one iocyanurate ring. The preparation of such polyisocyanates is described, for example, in EP-A-10,589, U.S. Pat. No. 4,324,879, herein incorporated by reference. The product described in Example 2 of this publication is particularly suitable.

The reaction product of components (a) and (b) to which the component (c) has been added is then freed from most of its free starting diisocyanate (a) by distillation in known manner. This distillative removal of the starting diisocyanate is preferably carried out in a thin layer distillation apparatus within the temperature range of about 150° to 180° C., more preferably about 160° to 180° C., and preferably at a pressure of about 0.1 to 0.5 mbar.

The virtually complete removal of the starting diisocyanate is made possible by the addition of the above-mentioned component (c) which contributes substantially to lowering the softening point and the fusion viscosity of the urethane group-containing polyisocyanate which has been freed from the monomer.

After the distillative treatment, the end products obtained as distillation residue generally contain less than 0.4% by weight, in most cases less than 0.3% by weight of free starting diisocyanates (a). The end products of the process are normally dissolved in inert solvents such as toluene, xylene, butyl acetate, ethyl acetate, methoxypropyl acetate, methyl ethyl ketone or any mixtures of such solvents to form about 60 to 80% by weight solutions. The proportion of free starting diisocyanate (a) present in these solutions may, if desired be reduced to less than about 0.2% by weight by the addition of an alcohol.

Suitable alcohols for this purpose include in particular low molecular weight monohydric and polyhydric alcohols such as methanol: ethanol; the isomeric propanols, butanols, pentanols and hexanols: and higher valent alcohols of the type already mentioned above as examples of component (b). Relatively high molecular weight alcohols such as octyl alcohol or lauryl alcohol may, of course, be used for the same purpose instead of the above-mentioned low molecular weight alcohols.

If an after-treatment is found to be advisable, the alcohols are added to the above-mentioned solutions in a quantity of up to about 0.7 equivalents of alcohol per kg of solvent-free distillation residue. The substantially selective urethanization of the remaining quantity of free starting diisocyanate (a) after the addition of this alcohol is generally carried out at room temperature or with mild heating of the solutions to temperatures up to about 50° C., preferably up to about 40° C.

The products obtained according to the invention are distinguished by their exceptionally low content in free starting diisocyanate, which is less than 0.3% by weight, preferably less than 0.2% by weight, and in most cases less than 0.15% by weight, and the high NCO content amounting to about 13 to 19% by weight, preferably about 13 to 18% by weight.

The products according to the invention are high quality "lacquer polyisocyanates" and are particularly suitable as reaction components for organic polyhydroxyl compounds in two-component polyurethane lacquers. Such two-component polyurethane lacquers are suitable in particular for coating textiles, leather, plastics, wood, paper or metals.

The invention is further illustrated but is not intended to be limited by the following examples in which all parts and percentages are by weight unless otherwise specified.

EXAMPLES

EXAMPLE 1

1287 g of a mixture of 65 parts by weight of 2,4-diisocyanatotoluene and 35 parts by weight of 2,6-diisocyanatotoluene were stabilized with 0.3 g of isophthaloyl chloride and heated to 80° C. A mixture of 83.1 g of trimethylolpropane and 40.3 g of diethylene glycol was added within one hour. The reaction mixture was stirred for 3 hours at this temperature, cooled to room temperature and mixed with 64.3 g of a polyisocyanate containing isocyanurate groups based on 1,6-diisocyanatohexane, having an isocyanate content of 21.5% by weight, containing 0.2% by weight of free 1,6-diisocyanatohexane and prepared according to Example 2 of EP-A-10,589. The resulting mixture was freed from the volatile constituents in a thin layer evaporator at a temperature of 160° C. and a pressure of 0.4 mbar. After dilution with 215 g of ethyl acetate, 860 g of a 75% solution of the polyisocyanate in ethyl acetate was obtained having a free diisocyanatotoluene content of 0.2% by weight, based on the quantity of solution. 7.5 g of methanol were then added to the solution and the solution was gently stirred at 30° C. for 10 hours.

A solution having a viscosity of 2750 mPa.s/23° C. was obtained. The solution had an NCO content of 12.5% and contained 0.05% of free diisocyanatotoluene.

EXAMPLE 2

860 g of a polyisocyanate solution prepared as in Example 1 were subjected to thin layer distillation and dissolved in ethyl acetate. 8.3 g of diethylene glycol were then added and the mixture was stirred at 50° C. for 6 hours.

A product having a viscosity of 3950 mPa.s/23° C. and an NCO content of 12.5% was obtained. The free TDI content was 0.06%.

EXAMPLE 3

1287 g of 2,4-diisocyanatotoluene were heated to 80° C. and a mixture of 83.1 g of trimethylolpropane and 40.3 g of diethylene glycol was added in the course of one hour. The reaction mixture was stirred for 3 hours at this temperature and then mixed with 64.3 g of the polyisocyanate containing isocyanurate groups mentioned in Example 1.

The excess diisocyanatotoluene was then distilled off in a thin layer evaporator at a temperature of 160° C. and a pressure of 0.4 mbar. After dilution with 215 g of ethyl acetate, 860 g of a 75% solution of the polyisocyanate in ethyl acetate was obtained. The solution contained 0.22% of free diisocyanatotoluene. After the addition of 6.1 g of methanol and stirring of the reaction mixture for 12 hours at 30° C., a solution containing 0.10% of free diisocyanatotoluene was obtained. The viscosity of the solution was 1700 mPa.s/23° C. and its isocyanate content was 13.0%.

EXAMPLE 4

860 g of a polyisocyanate solution prepared by a method analogous to that of Example 3 was subjected to thin layer distillation, dissolved in ethyl acetate and then reacted with 12.2 g of methanol for 12 hours at 30° C.

A product having a viscosity of 2600 mPa.s/23° C. and an isocyanate content of 11.83% was obtained The free TDI content was 0.05%.

EXAMPLE 5

1287 g of a mixture of 65 parts by weight of 2,4-diisocyanatotoluene and 35 parts by weight of 2,6-diisocyanatotoluene were stabilized with 0.3 g of benzoyl chloride and heated to 90° C. A mixture of 73.7 g of trimethylpropane and 50.9 g of diethylene glycol was added in the course of one hour.

The reaction mixture was stirred at this temperature for 2¼ hours, cooled to room temperature and mixed with 30.5 g of the polyisocyanate containing isocyanurate groups mentioned in Example 1. The volatile constituents of this mixture were distilled off in a thin layer evaporator at a temperature of 160° C. and a pressure of 0.35 mbar.

After dilution with 203 g of ethyl acetate 810 g of a 75% solution of the polyisocyanate in ethyl acetate was obtained having a free diisocyanatotoluene content of 0.24% by weight, based on the quantity of solution.

Reaction of this solution with a mixture of 9.7 g of dipropyleneglycol and 24.2 g of lauryl alcohol at 30° C. for 20 hours yielded a product having a viscosity of 3500 mPa.s/23° C. and an isocyanate content of 11.5%. The free TDI content was 0.12%.

EXAMPLE 6

830 parts by weight of trimethylolpropane and 509 parts by weight of dipropylene glycol were added at 50° to 60° C. to 1287 parts by weight of 2,4-diisocyanatotoluene. The temperature rose to 80° C. during this addition and was kept at this level for 5 hours with vigorous stirring. At the end of this time, the isocyanate content of the clear liquid obtained was 35 8% (calculated 36%). 10% by weight of this substance was separated off and worked up separately. To the major portion of the liquid were added 53 parts by weight of the polyisocyanate containing isocyanurate groups from Example 1.

Excess 2,4-diisocyanatotoluene was then removed using a molecular evaporator with pre-evaporator at 160° C. and 0.3 mbar. A solid, clear resin was obtained and dissolved in ethyl acetate to form a 75% solution. The isocyanate content of the solution was 13.5% and the free diisocyanate content was 0.12% (solution 6 a).

The separated portion of liquid to which no polyisocyanate from Example 1 had been added was then also distilled under the same conditions and dissolved in ethyl acetate to form a 75% solution. This solution had an isocyanate content of 13.1% and a free diisocyanate content of 0.4% by weight (solution 6 b).

Various hydroxyl compounds were now added to 100 g portions of the solutions, vigorously mixed and left to stand for 24 hours at about 30° C. The free TDI contents were then again determined. The results are summarized in the following Table.

| | 100 g of Solution 6a | | | 100 g of Solution 6b | | |
| --- | --- | --- | --- | --- | --- | --- |
| | Isocyanate content | Monomeric TDI content | Viscosity mPas/23° C. | Isocyanate content | Free TDI content | Viscosity mPas/23° C. |
| + 0.37 g isobutanol | 13.2% | 0.10% | 1200 | 12.6% | 0.32% | 1600 |
| + 0.3 g isopropanol | 13.1% | 0.05% | 1000 | 12.7% | 0.28% | 1500 |
| + 0.335 g dipropylene glycol | 12.8% | 0.07% | 1300 | 12.1% | 0.32% | 2100 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a urethane group-containing polyisocyanate which contains not more than 0.4% of monomeric starting diisocyanate, based on the weight of said polyisocyanate, which comprises
   (i) forming a urethane group-containing reaction product by reacting
      (a) an excess quantity, based on the equivalents of component (b), of a diisocyanate component comprising at least one aromatic diisocyanate which is free from urethane groups with
      (b) a polyol component comprising at least one polyhydric alcohol having a molecular weight of 62 to 250,
   (ii) adding about 0.3 to 10% by weight, based on the weight of said urethane group-containing reaction product, of
      (c) an aliphatic polyisocyanate containing isocyanurate groups,
   (iii) distilling the mixture formed in accordance with step (ii) to remove monomeric diisocyanate and
   (iv) optionally adding up to about 0.5 equivalents of an alcohol per kg of solvent-free distillation residue to further reduce the amount of monomeric diisocyanate.

2. The process of claim 1 wherein component (a) comprises 2,4-diisocyanatotoluene or mixtures with 2,6-diisocyanatotoluene.

3. The process of claim 1 wherein component (b) comprises a mixture of at least one aliphatic diol and at least one aliphatic triol in a molar ratio of about 1:2 to 1:0.5.

4. The process of claim 2 wherein component (b) comprises a mixture of at least one aliphatic diol and at least one aliphatic triol in a molar ratio of about 1:2 to 1:0.5.

5. The process of claim 1 wherein component (c) comprises N,N,N-tris-(isocyanatohexyl)-isocyanurate.

6. The process of claim 2 wherein component (c) comprises N,N,N-tris-(isocyanatohexyl)-isocyanurate.

7. The process of claim 3 wherein component (c) comprises N,N,N-tris-(isocyanatohexyl)-isocyanurate.

8. The process of claim 4 wherein component (c) comprises N,N,N-tris(isocyanatohexyl)-isocyanurate.

* * * * *